United States Patent
Mcmillan et al.

(10) Patent No.: US 7,548,308 B2
(45) Date of Patent: Jun. 16, 2009

(54) ILLUMINATION ENERGY MANAGEMENT IN SURFACE INSPECTION

(75) Inventors: Wayne Mcmillan, San Jose, CA (US); Christian Wolters, Campbell, CA (US)

(73) Assignee: KLA-Tencor Corporation, San Jose, CA (US)

( * ) Notice: Subject to any disclaimer, the term of this patent is extended or adjusted under 35 U.S.C. 154(b) by 140 days.

(21) Appl. No.: 11/127,280

(22) Filed: May 11, 2005

(65) Prior Publication Data

US 2006/0256325 A1 Nov. 16, 2006

(51) Int. Cl.
*G01N 21/00* (2006.01)
(52) U.S. Cl. .................................................. 356/237.2
(58) Field of Classification Search ................. 356/23, 356/445–448, 337–343, 213, 218, 237.1–241.6, 356/375, 237.2, 608, 609; 359/227–324; 250/459.1; 355/53; 438/7, 16
See application file for complete search history.

(56) References Cited

U.S. PATENT DOCUMENTS

| | | | |
|---|---|---|---|
| 4,585,348 A | 4/1986 | Chastang | |
| 4,870,631 A | 9/1989 | Stoddard | |
| 4,873,430 A | 10/1989 | Juliana | |
| 5,189,481 A | 2/1993 | Jann | |
| 5,270,794 A | 12/1993 | Tsuji | |
| 5,289,263 A * | 2/1994 | Kiyokawa et al. | 356/615 |
| 5,293,216 A | 3/1994 | Moslehi | |
| 5,377,002 A * | 12/1994 | Malin et al. | 356/237.2 |
| 5,416,594 A | 5/1995 | Gross | |
| 5,486,264 A * | 1/1996 | Ghandour | 438/746 |
| 5,586,040 A * | 12/1996 | Baumgart et al. | 700/166 |
| 5,610,897 A | 3/1997 | Yamamoto | |
| 5,633,747 A | 5/1997 | Nikoonahad | |
| 5,644,562 A | 7/1997 | de Groot | |
| 5,798,829 A * | 8/1998 | Vaez-Iravani | 356/237.1 |
| 5,864,394 A | 1/1999 | Jordan | |
| 5,880,838 A | 3/1999 | Marx | |
| 5,895,915 A * | 4/1999 | DeWeerd et al. | 250/234 |
| 5,903,342 A | 5/1999 | Yatsugake | |
| 5,936,726 A * | 8/1999 | Takeda et al. | 356/237.2 |
| 5,985,689 A | 11/1999 | Singhal | |
| 5,986,763 A | 11/1999 | Inoue | |
| 5,995,226 A | 11/1999 | Abe | |
| 6,081,325 A * | 6/2000 | Leslie et al. | 356/237.2 |
| 6,108,079 A * | 8/2000 | Maeshima et al. | 356/237.2 |
| 6,154,270 A * | 11/2000 | Ozawa | 355/53 |
| 6,341,180 B1 * | 1/2002 | Pettersson et al. | 382/255 |
| 6,710,295 B1 * | 3/2004 | Tam et al. | 219/121.85 |
| 7,027,640 B2 * | 4/2006 | Park et al. | 382/152 |
| 7,031,796 B2 * | 4/2006 | Lange | 700/123 |
| 2002/0018189 A1 * | 2/2002 | Mulkens et al. | 355/30 |
| 2002/0034152 A1 * | 3/2002 | Kumasaka et al. | 369/272 |

(Continued)

*Primary Examiner*—Tarifur Chowdhury
*Assistant Examiner*—Jonathan M Hansen
(74) *Attorney, Agent, or Firm*—Luedeka, Neely & Graham, P.C.

(57) ABSTRACT

An apparatus and associated method for reducing thermal damage on a specimen during an inspection which includes a radiation source for supplying a beam of radiation, and a means for adjusting a first energy level of the beam of radiation to a second energy level as the beam of radiation is variably positioned from a first location on the surface of the wafer to a second location on the surface of the wafer.

6 Claims, 3 Drawing Sheets

U.S. PATENT DOCUMENTS

| | | | |
|---|---|---|---|
| 2002/0125230 A1* | 9/2002 | Haight et al. | 219/121.69 |
| 2003/0160184 A1* | 8/2003 | Curry et al. | 250/459.1 |
| 2004/0021976 A1* | 2/2004 | Deeman et al. | 360/75 |
| 2004/0075882 A1* | 4/2004 | Meisburger | 359/290 |
| 2004/0160583 A1* | 8/2004 | Hubertus Mulkens et al. | 355/30 |
| 2005/0062963 A1* | 3/2005 | Yoshida et al. | 356/237.5 |

* cited by examiner

FIG._1

ILLUMINATION ENERGY MANAGEMENT IN SURFACE INSPECTION

BACKGROUND

The subject matter described herein relates to surface inspection, and more particularly to illumination energy management in surface inspection.

As design rules and process windows continue to shrink, integrated circuit (IC) manufacturers face challenges in achieving and maintaining yields and profitability while moving to new processes. The challenges have become more difficult because inspection systems are required to capture a wider range of physical defects on wafer surfaces. One such inspection system includes the use of lasers, which provide high sensitivity to detect small defects, and a relatively high throughput.

Lasers can cause surface damage to a semiconductor wafer, e.g., from thermal shock from the laser during a surface inspection process. In some inspection systems the wafer rotates about a central axis during the inspection process. Hence, the wafer surface near the central axis moves at a slower velocity than the wafer surface near the outer edge of the wafer. Accordingly, damage tends to occur near radial inner portions of a wafer surface because relatively more energy/mm$^2$ is imparted to the inner surface.

SUMMARY

Described herein are systems and accompanying methods for managing the amount of laser power applied to the surface of a semiconductor wafer during a surface inspection process.

In one aspect, the laser power can be adjusted as a continuous or discrete function of the radial distance of the laser beam spot from the center of the wafer.

In another aspect, a filter may be interposed between the laser origin and the wafer, such that the filter attenuates a portion of the laser power that varies as a function of the radial distance of the laser beam spot from the center of the wafer.

In yet another aspect, laser power can be managed by varying the spot size of the radiation beam incident on the surface of the wafer as a function of radial distance of the laser beam spot from the center of the wafer or by varying the speed of rotation of the wafer as a function of the radial distance of the laser beam spot from the center of the wafer.

Additional aspects are set forth in part in the detailed description which follows. It is to be understood that both the foregoing general description and the following detailed description are merely exemplary, and are intended to provide an overview or framework for understanding the nature and character of the invention as it is claimed.

BRIEF DESCRIPTION OF THE DRAWINGS

The detailed description is described with reference to the accompanying FIGS. In the FIGS, the left-most digit(s) of a reference number identifies the FIG in which the reference number first appears. The use of the same reference numbers in different FIGS indicates similar or identical items.

DETAILED DESCRIPTION

Described herein are exemplary systems and methods for illumination energy management in surface inspection. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

Figure 1:
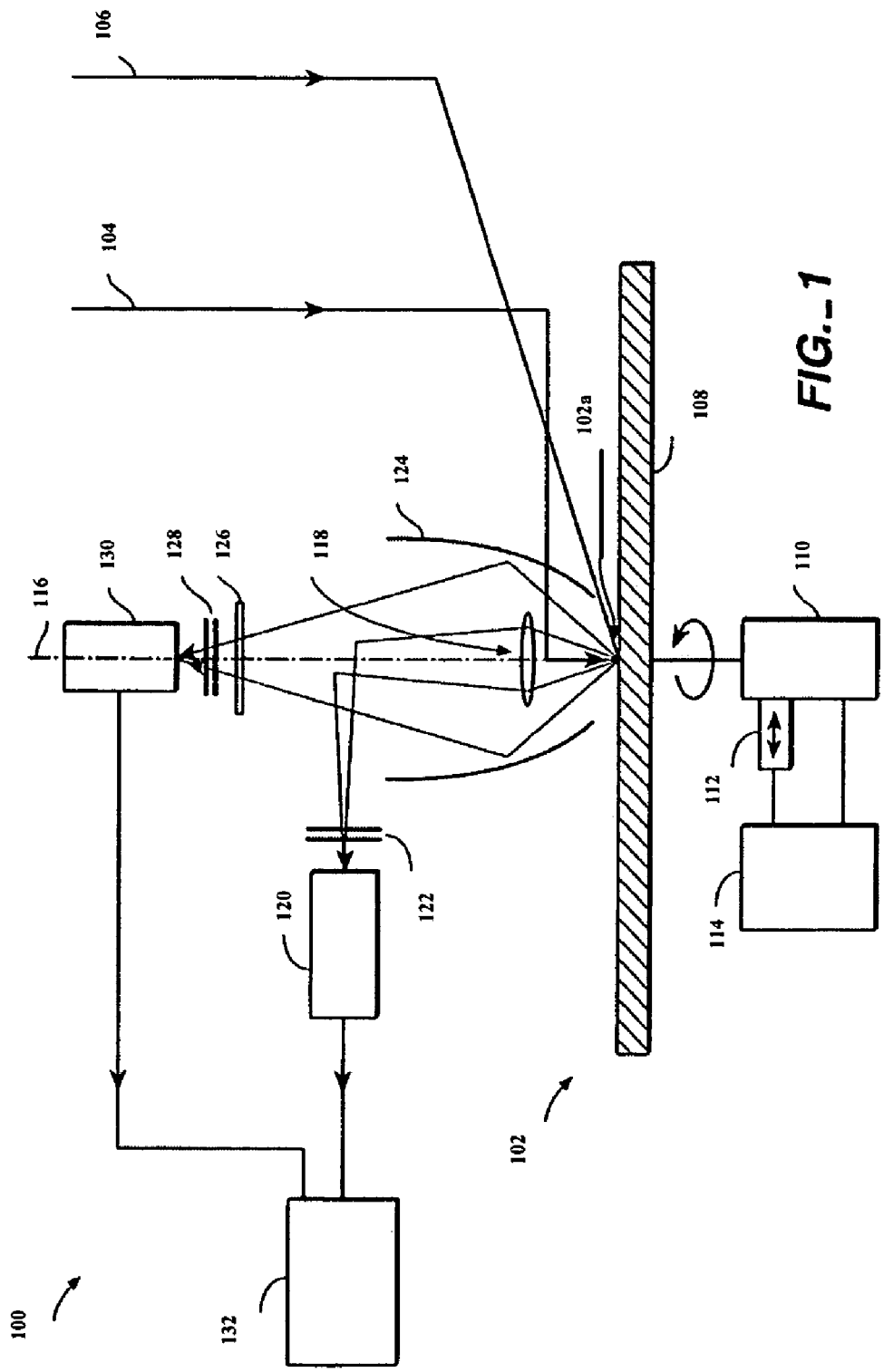
FIG. 1 is a simplified schematic illustration of one embodiment of a surface inspection system.

FIG. 1 is a simplified schematic view of a typical surface inspection system 100. To simplify FIG. 1, some of the optical components of the system have been omitted, such as components directing the illumination beams to the wafer. A wafer 102 is illuminated by a normal incidence beam 104 and/or an oblique incidence beam 106. Wafer 102 is supported on a chuck 108 which is rotated by means of a motor 110 and translated in a direction by gear 112 so that beams 104 and/or 106 illuminate an area or spot 102a which is caused to move and trace a spiral path on the surface of wafer 102 to inspect the surface of wafer 102. Motor 110 and gear 112 are controlled by controller 114 in a manner known to those skilled in the art.

The area or spot 102a illuminated by either one or both beams 104, 106 on wafer 102 scatters radiation from the beam(s). The radiation scattered by area 102a along directions close to a line 116 perpendicular to the surface of the wafer and passing through the area 102a is collected and focused by lens collector 118 and directed to a photo-multiplier tube (PMT) 120. Since lens 118 collects the scattered radiation along directions close to the normal direction, such collection channel is referred to herein as the narrow channel and PMT 120 as the dark field narrow PMT. When desired, one or more polarizers 122 may be placed in the path of the collected radiation in the narrow channel.

Radiation scattered by spot 102a of wafer 102, illuminated by either one or both beams 104, 106, along directions away from the normal direction 116 is collected by an ellipsoidal collector 124 and focused through an aperture 126 and optional polarizers 128 to dark field PMT 130. Since the ellipsoidal collector 124 collects scattered radiation along directions at wider angles from the normal direction 116 than lens 118, such collection channel is referred to as the wide channel. The outputs of detectors 120, 130 are supplied to a computer 132 for processing the signals and determining the presence of anomalies and their characteristics.

Various aspects of surface inspection system 100 are described in U.S. Pat. No. 6,271,916 and U.S. Pat. No. 6,201,601, both of which are incorporated herein by reference. An exemplary surface inspection system is available from KLA-Tencor Corporation of San Jose, Calif., the assignee of the present application.

Figure 2:
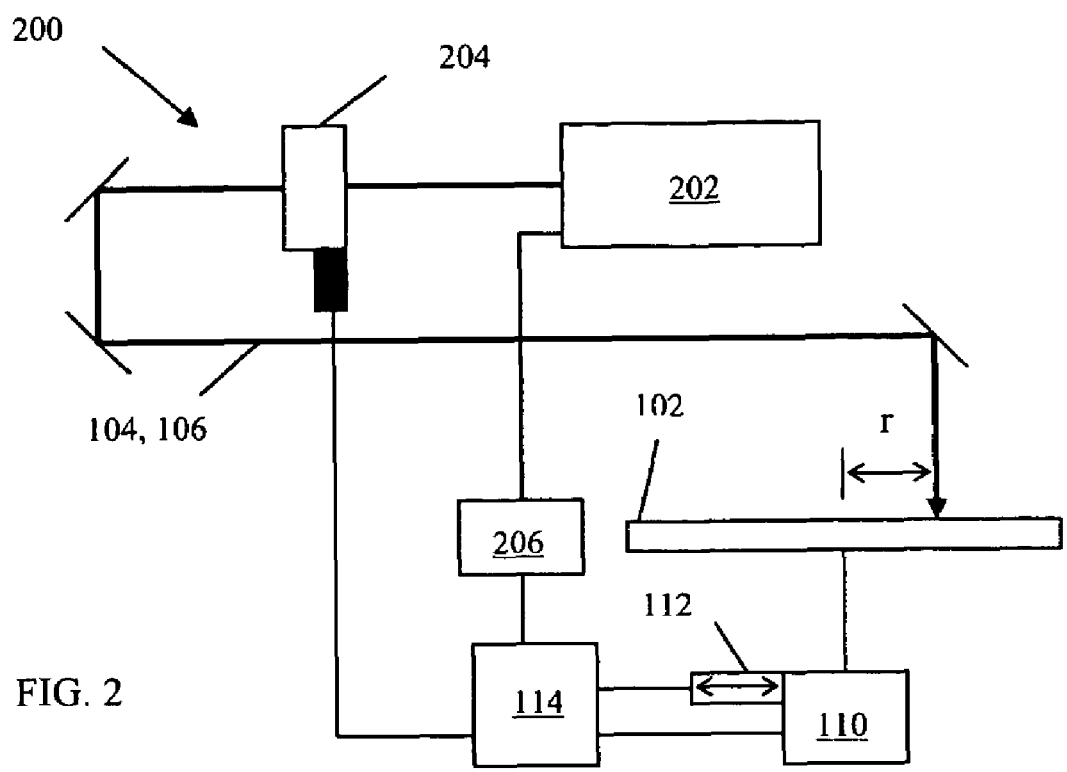
FIG. 2 is a simplified schematic illustration of components of one embodiment of a radiation management apparatus.

FIG. 2 is a simplified schematic illustration of optical components 200 of surface inspection system 100 in accordance with an embodiment. It should be understood that optical components 200 can be included and integrated into surface inspection system 100, with only the modifications necessary to encompass embodiments described herein. For clarity, some components of the surface inspection system have been omitted from FIG. 2.

Optical components 200 of surface inspection system 100 direct illumination beam(s) 104, 106 to wafer 102. Accordingly, optical components 200 include at least one radiation light source, such as a laser 202, and a filter or attenuator 204 that controls the energy level of incidence beam(s) 104, 106 that are delivered to wafer 102. As discussed in more detail below, in one embodiment, motion controller 114 controls the variable positioning of attenuator 204 to set the energy level of the laser power in system 100. Motor 110 and gear 112 are also controlled by motion controller 114 to rotate and translate wafer 102 as appropriate to achieve the proper scanning motion.

Although FIG. 2 depicts a single laser 202, a greater number of lasers may be included among optical components 200, as appropriate for a particular application. Further, alternative radiation light sources, such as, for example, xenon lamps, light-emitting-diodes and the like, may be used instead of laser 202.

Attenuator 204 may be, for example, an addressable array of selected neutral fixed-density filters; a continuously variable neutral density filter; a plurality of polarizers that includes at least one rotatable polarizer; a rotating polarization retarder placed in front of a polarizer and the like, all of which are known in the art. Beam 106 passes through attenuator 204, which produces an attenuated, collimated beam with a desired power level.

Referring now to FIG. 2 in one operational embodiment, the dosage or energy level D of laser 202 is automatically adjusted as a function of the radial scan distance of the laser beam spot or scan spot from the center of wafer 102. As illustrated in Equation 1, with a given laser power P, wafer rotational speed $\omega$, and wafer translational speed $V_x$, dosage D (light power density×exposure time) is approximately proportional to:

$$P/(\omega \times r + V_x) \quad (1)$$

where r is equal to the current scan radius of the scan spot from the center of wafer 102. The effective dosage D, therefore, increases as the radius of the scan radius decreases, thus reaching a maximum at r=0.

In accordance with one embodiment, as the scan radius r approaches 0, the laser power P is simultaneously ramped down. In operation, laser controller 206 of surface inspection system 100 can be made to drive laser 202 in a laser power feedback loop, thus ramping a laser power profile as a function of scan radius r. Alternatively, a calibration table can be provided from which a correction factor for discrete scan radius can be determined. The calibration table can be system specific.

The loss of signal and thus the potential loss of signal/noise ratio (S/N) is compensated by a simultaneously adjustable noise filter and amplitude correction. The S/N can be determined as set forth in Equation 2, where $R_t$ is equal to the tangential spot size and $R_r$ is equal to the radial spot size.

$$\frac{\text{Signal}}{\text{Noise}} \propto \sqrt{\frac{P}{R_t \times \omega \times r}} \times \frac{1}{R_r} \quad (2)$$

In this embodiment, a constant S/N, that is, a constant energy level, can be maintained while ramping down laser power P in approximate proportion to scan radius r, if $R_r$, $R_t$, $\omega$ are maintained as a constant. That is:

$$P \propto r \quad (3)$$

It has been shown that the maximum dosage D may be reduced by a factor of up to 10 as the scan radius r approaches 0 without negatively affecting the sensitivity of surface inspection system 100.

In another embodiment, dosage D can be adjusted by varying the rotational speed $\omega$ of the wafer as a function of the radial distance of the beam spot from the center of the wafer. As shown in Equation 4, if P, $R_r$, $R_t$ are maintained constant, then rotational speed $\omega$ is approximately proportional to the scan radius from the center of wafer 102 as follows:

$$\omega \propto \frac{1}{r} \quad (4)$$

Accordingly, in operation, controller 114 can cause the speed of motor 110 to vary the rotational speed of wafer 102, while simultaneously translating wafer 102 under incidence beam(s) 104, 106. In this manner, as r approaches 0, the rotational speed of wafer 102 increases to reduce the energy/mm² imparted to the inner surface of wafer 102.

In another embodiment, dosage D can be adjusted by varying the spot size as a function of the radial distance of the beam spot from the center of wafer 102. As shown in Equation 5, if P, $R_r$, $\omega$ are maintained constant, then spot size $R_t$ is approximately proportional to the scan radius from the center of wafer 102 as follows:

$$R_t \propto \frac{1}{r} \quad (5)$$

Accordingly, in operation, laser controller 206 can operate to continuously refocus laser beam(s) 104, 106 using a focusing device, such as a lens assembly and the like, to cause the spot size of the beam to vary. In this manner, as r approaches 0, the spot size can be increased to reduce the energy/mm² imparted to the inner surface of wafer 102.

In some embodiments, dosage D is adjusted by interposing a filter or attenuator 204 between the laser origin and wafer 102, where the filter attenuates a portion of the laser power that varies as a function of the radial distance of the beam spot from the center of wafer 102.

In one operational embodiment, attenuator 204 of surface inspection system 100 can be configured for the selection of or conditioning of filters, polarizers, and the like, to pass or reject specific wavelengths to set appropriate attenuation levels. In this embodiment, scan motion can be synchronized with attenuation value and proper amplitude correction, such that dosage D is automatically adjusted as a discrete function of the radial distance r of the scan spot from the center of wafer 102.

In another operational embodiment, attenuator 204 is motorized such that it can be variably positioned by motion controller 114 between laser 202 and wafer 102. In this manner, incidence beam(s) 104, 106 travels through attenuator 204 as the beam is delivered to wafer 102. By manipulating and thus varying the distance of attenuator 204 from the origin or source of the radiation from laser 202, the power level of beam(s) 104, 106 is also made variable. In this embodiment, scan motion can be synchronized with attenuation value and proper amplitude correction, such that as the scan radius r approaches 0, the proper attenuation value is provided by the adjustment of the position of attenuator 204 relative to laser 202.

Figure 3:
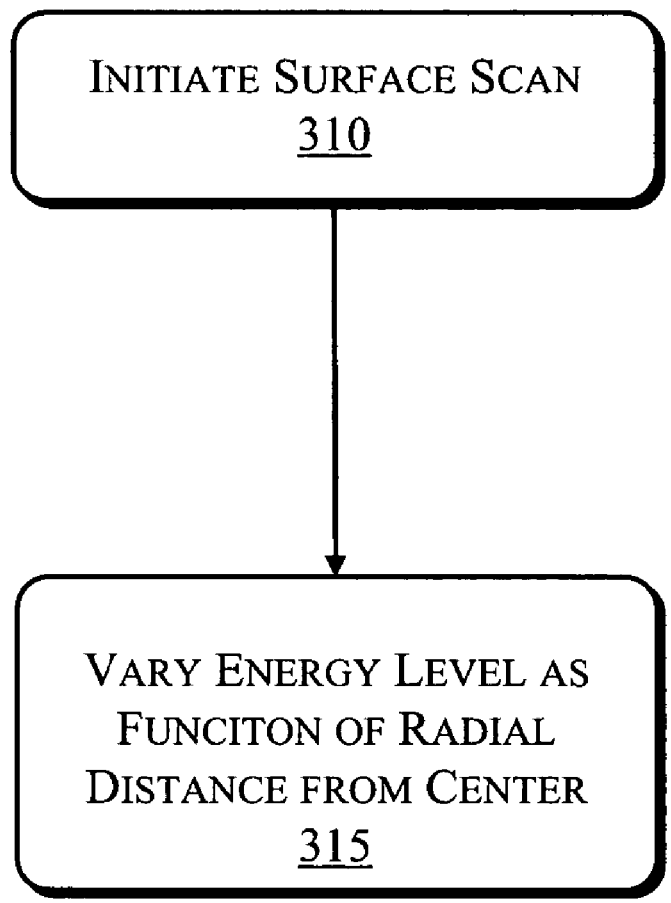
FIG. 3 is a flowchart representing one embodiment of a method for managing radiation during an inspection process.

FIG. 3 is a flowchart which provides a general method for managing the radiation or laser power by employing the various embodiments described herein. Referring to FIG. 3, at operation 310 a surface scan is initiated. In various embodiments initiating a surface scan includes causing a surface of a wafer to be impinged by a beam of radiation at a first location such that the beam of radiation imparts a first level of energy to the surface. At operation 315 the radiation energy level imparted to the surface is varied as a function of the radial distance from the center of the wafer as the radiation beam moves from the first location on the surface of the wafer to a second location on the surface of the wafer.

In one embodiment, varying the energy level includes varying the power level of the radiation beam as a function of radial distance of the radiation beam from the center of the wafer.

Alternatively, varying the energy level may include varying the speed of rotation of the wafer as a function of the radial distance of the radiation beam from the center of the wafer, or varying a spot size of the radiation beam as a function of radial distance of the radiation beam from the center of the wafer.

In another alternative embodiment, adjusting the first energy level to the second energy level includes varying the position of a filter relative to the origin of the radiation beam as a function of radial distance of the radiation beam from the center of the wafer.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A method for managing radiation comprising:
   causing a surface of a wafer to be impinged by a beam of radiation at a first location with a first energy level; and
   adjusting said first energy level to a second energy level as said beam of radiation moves from said first location on said surface of said wafer to a second location on said surface of said wafer, wherein said adjusting said first energy level to said second energy level comprises varying the speed of rotation of the wafer as a function of the radial distance of the beam of radiation from the center of the wafer.

2. The method of claim 1, wherein said adjusting said first energy level to said second energy level comprises further varying the power level of the beam of radiation as a function of radial distance of the beam of radiation from the center of the wafer.

3. The method of claim 1, wherein said adjusting said first energy level to said second energy level comprises further varying the position of a filter relative to the origin of the beam of radiation as a function of radial distance of the beam of radiation from the center of the wafer.

4. The method of claim 1, wherein said beam of radiation emanates from a laser.

5. The method of claim 1, wherein said beam of radiation emanates from a source taken from the group consisting of xenon lamps and light-emittingdiodes.

6. The method of claim 1, further comprising implementing a signal to noise ratio compensation filter routine to maintain a constant signal to noise ratio as the radiation beam is adjusted from the first energy level to the second energy level, wherein the signal to noise ratio is calculated using a formula:

$$\frac{\text{Signal}}{\text{Noise}} \propto \sqrt{\frac{P}{R_t \times \omega \times r}} \times \frac{1}{R_r}$$

where:
P = Laser power
$R_r$ = Radial spotsize
$R_t$ = Tangential spotsize
ω = rotation speed
r = current scan radius.

* * * * *